United States Patent [19]
Gubernick et al.

[11] Patent Number: 5,905,265
[45] Date of Patent: *May 18, 1999

[54] METHOD OF IMPROVING SKIN CONDITION

[75] Inventors: Joseph Gubernick; Gheorghe Cioca, both of New York, N.Y.

[73] Assignee: EL Management Corp., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/646,798

[22] Filed: May 21, 1996

[51] Int. Cl.[6] .................................................. H01J 37/00
[52] U.S. Cl. ............................................................ 250/492.1
[58] Field of Search ......................................... 250/492.1

[56] References Cited

U.S. PATENT DOCUMENTS

| | | | |
|---|---|---|---|
| 5,012,110 | 4/1991 | Kropp | 250/492.1 |
| 5,138,172 | 8/1992 | Kropp | 250/492.1 |
| 5,247,179 | 9/1993 | Tachibana | 250/492.1 |
| 5,543,111 | 8/1996 | Bridges et al. | 250/492.1 |

*Primary Examiner*—Kiet T. Nguyen
*Attorney, Agent, or Firm*—Pennie & Edmonds LLP

[57] ABSTRACT

The present invention provides a method of improving skin condition by administering to the skin a physiologically acceptable substrate that is exposed to a magnetic vector potential field and that optionally contains information energy.

14 Claims, 3 Drawing Sheets

METHOD OF IMPROVING SKIN CONDITION

FIELD OF THE INVENTION

The present invention relates to the field of homeopathic treatments, and more particularly, to the use of a physiologically acceptable substrate containing information energy for cosmetic and medical applications.

BACKGROUND OF THE INVENTION

Homeopathy has been explained as copying information, e.g., a pattern or a combination of oscillations of different frequencies, onto a substrate from the information or pattern existing in the molecular structure of natural substances, e.g., herbs, antibodies, or pollen. The substrate with the copied information or pattern incorporated therein can then be used to effect a desired response. For example, in homeopathic medicine, the desired response might be the reduction of allergy symptoms in hay fever sufferers.

U.S. Pat. No. 5,138,172 of K. E. Werner Kropp teaches a method for applying information energy to a substrate such as saline solution or oil by exposing the substrate to a magnetic vector potential field. U.S. Pat. No. 5,012,110 of K. E. Werner Kropp teaches a process for the manufacture of a synthetic homeopathic substrate by placing the substrate between opposing sets of magnets.

French patent application, Publication No. 2,634,381, published Jan. 26, 1990 and WO 91.10450, published Jul. 25, 1991 of J. J. C. Morez teach a method of producing larger quantities of homeopathic medicine by transferring to a large mass of material such as water the electromagnetic information of a homeopathic remedy by way of a transmitter-receiver.

An object of the present invention is to provide a novel method of using physiologically acceptable substrates containing information energy for use in cosmetics, e.g. for improving skin condition.

Another object of the present invention is to provide a novel method of using physiologically acceptable substrates containing information energy for use in homeopathic medicine.

SUMMARY OF THE INVENTION

The invention is related to the use of substrates such as aqueous salt solutions, massage oils or other pharmaceutically acceptable carriers that have been exposed to information energy such as oscillation patterns modeled after those found in natural herbs. In general, the substrate can be in the gaseous, liquid, solid or liquid crystalline phase. The aqueous salt solutions may contain sodium chloride and magnesium chloride; as well as dissolved iron and calcium ions.

The substrates that contain information energy can be used to improve skin condition by topically administering the substrates to skin. By skin condition, we mean, without limitations, dry skin, xerosis, ichthyosis, dandruff, brownish spots, keratoses, melasma, lentigines, age spots, liver spots, pigmented spots, wrinkles, blemishes, skin lines, oily skin, acne, warts, eczema, pruritic skin, psoriasis, inflammatory dermatosese disturbed keratinization, skin changes associated with aging, nail or skin requiring cleansers, conditioning or treatment, and hair or scalp requiring shampooing or conditioning.

The present invention provides a specific method of increasing proline uptake in human dermal fibroblast cells by contacting the cells with a physiologically acceptable substrate that contains information energy.

Increased proline uptake is an indication of the collagen synthesis of these cells—a desirable cosmetic benefit which is one route of improving skin condition. Fibroblast cells, which are located in the dermis, perform many functions, i.e., synthesize collagen, elastin, glycoseaminoglycans (GAGS), to name a few. Proline is an amino acid which is an integral part of the collagen structure. By demonstrating an increase in the total amount of proline uptake, we demonstrate an increase in the total amount of collagen synthesized. Collagen and elastin are two proteins found in the dermis responsible for the firmness and elasticity of the skin. Young, healthy skin has an abundance of these two proteins. As the body ages, the process of synthesizing these proteins decreases. Therefore, the total amount of collagen/elastin diminishes in older, less healthy skin. Increasing the amount of collagen/elastin in the dermis by the present invention leads to improvement in skin condition.

The present invention further provides a specific method of producing the physiologically acceptable substrate that contains information energy. The method is generally described in U.S. Pat. Nos. 5,012,110 and 5,138,172 of K. E. Werner Kropp and comprises imparting information energy of desired frequencies to a substrate that has been placed in a specific configuration within a magnetic field, called a magnetic vector potential field. The apparatus for applying the information energy to the substrate may comprise a) two opposite sets of magnets, each said set of magnets comprising a plurality of magnets arranged side by side, with alternating N and S poles, wherein the substrate is exposed to a magnetic vector potential field when the substrate is placed between the opposing sets of magnets; and b) a means for applying information energy to the substrate when the substrate is located in the magnetic vector potential field.

The application of information energy to the substrate may be accomplished by exposing the substrate to the following Wekroma rods having the following properties:

1200.7 Antioxidants BHT N-acetyilcystine Beta Caratene

622 Cellulite

232 Revitalization Collagen Synthesis, Balancing Rods

7509 Neutralize Free Radicals

326 Inhibit Bacterial Growth

329 Inhibit Bacterial Growth

Fibro 1 stimulate fibroblast calls

Fibro 2 Stimulate fibroblast cells

Preferably, the substrate is exposed to the above Wekroma Rods by the use of a Wekroma Bio-Transfer device, wherein the substrate is at least once passed through such device. The substrate may be exposed to the rods individually or in combination.

The present invention additionally provides a method of improving skin condition comprising a) exposing a physiologically acceptable substrate to a magnetic vector potential field; and b) administering to the skin the exposed substrate. Thus, exposure of a substrate to a magnetic vector potential field, such as the sets of magnets described above without application of information energy is sufficient to obtain a treated substrate capable of improving skin condition. One preferable way of treating the substrate with a magnetic vector potential field is to pass the substrate at least once through the Wekroma Bio-Transfer device, without the placement of any Wekroma Rods within the device.

DETAILED DESCRIPTION OF THE PREFERRED EMBODIMENTS

The manner in which a substrate is exposed to information energy is generally described in U.S. Pat. No. 5,138,172 of K. E. Werner Kropp; U.S. Pat. No. 5,012,110 of K. E. Werner Kropp, French patent application, Publication No. 2,634,381 of J. J. C. Morez, and WO 91,10450 of J. J. C. Morez. The substrate is generally in a gaseous, liquid, solid or liquid crystalline phase.

Figure 1:
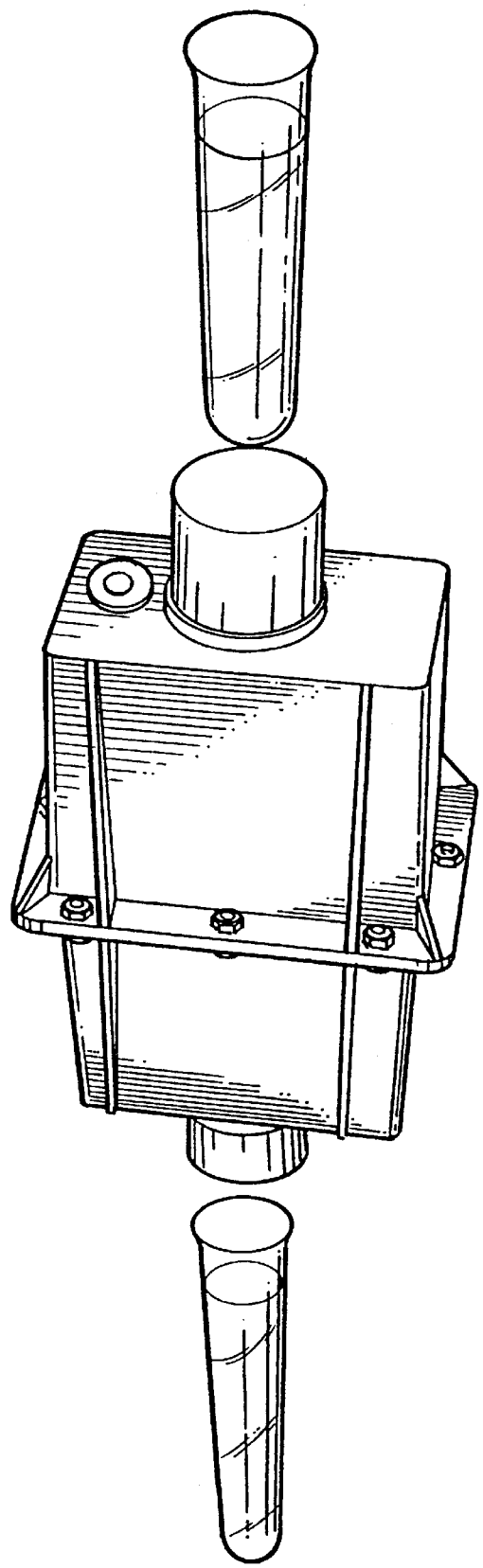
FIG. 1 depicts the Bio-Transfer device available from Wekroma-Vertrieb Schweiz.

One arrangement for exposing aqueous solutions to information energy is by use of a Wekroma Bio-Transfer device, purchased from Wekroma-Vertrieb Schweiz, Beat Lanz, 6313 Menzingen, Federal Republic of Germany. Rod No. 232 as supplied by Wekroma was placed in the Wekroma Bio-Transfer device as shown in FIG. 1. Test tubes containing aqueous solutions were passed through the Bio-Transfer device by way of a channel opening. The residence time the solution is in the Bio-Transfer device does not appear to be critical, typically ranging from less than one second to a few seconds. The rate at which the test tubes pass through the Bio-Transfer device is typically the speed at which they free fall. Both residence time and rate of pass through may be controlled by having the solution pump through the Bio-Transfer device at a certain controlled velocity.

Figure 3:
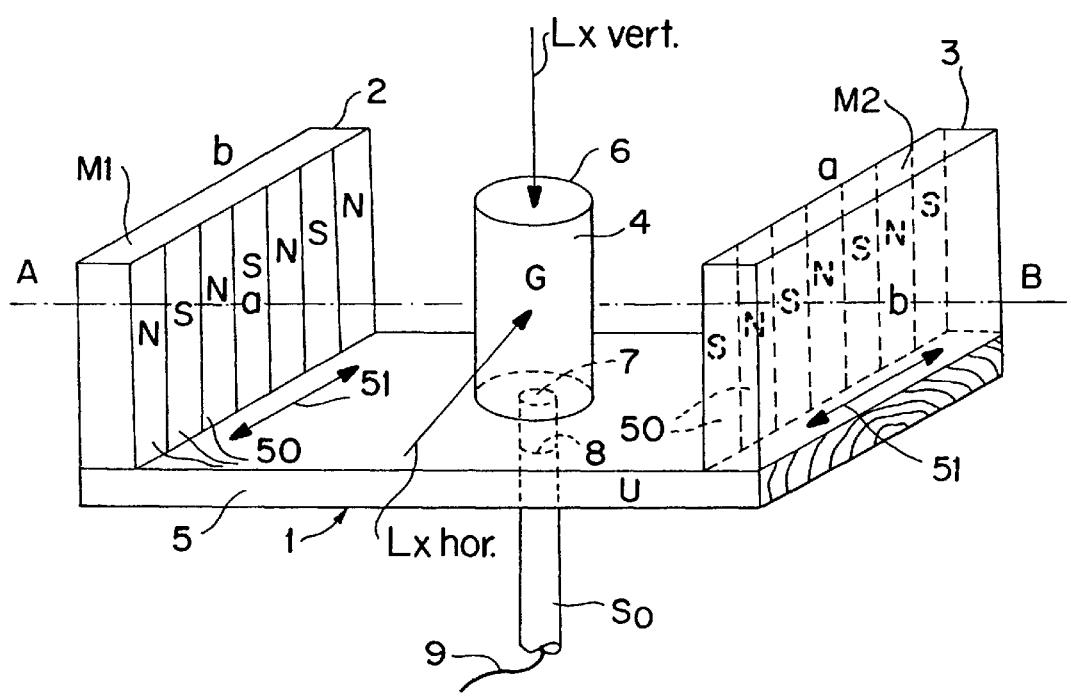
FIG. 3 is a diagrammatic perspective view of an apparatus for conducting ate processes according to the invention, wherein the permanent magnets are subdivided into individual striplike magnets with alternating North-South poles.

The basic arrangement for the treatment of liquids as substrates with a variation in the absorption properties thereof in a magnetic field is shown in FIG. 3. The magnetic field strength Ha is produced by permanent magnets 2 and 3 which are disposed in mutually opposite relationships in an opposite-pole configuration, on non-magnetic support 5. Disposed approximately in the middle of the arrangement is a glass vessel 6 with a substrate 4 to be treated, in the form of a liquid. The respectively selected information energy is supplied to the liquid in the glass vessel 6, perpendicularly to the orientation of the magnetic field Ha, by way of a probe So or 8, 7. In that connection, the glass vessel 6 may also be closed.

The magnetic longitudinal axes A and B of the two permanent magnets 2 and 3 are oriented in the same direction relative to each other. The probe So may be brought in either beside the substrate 4 or the vessel thereof (FIG. 3; 8) or through the non-magnetic support 5 to the substrate, from below (FIG. 3; 7). The information energy is supplied to the probe So by way of the connection 9.

In the embodiment shown, each individual magnetic strip 50 is also opposed by the alternative pole. By the use of a parallel swinging effect (see arrows 51), such polarity arrangement can be easily changed, for example, by arranging the same poles facing each other. Such a sidewise, offset, swinging, pole-changing arrangement can be performed even with high frequencies.

The arrows Lx vert(ical) and Lx hor(izontal) demonstrate the penetration direction of a laser beam as the carrier of the information.

EXAMPLE 1

The following demonstrates how aqueous saline solution treated with the Wskroma Bio-Transfer device can stimulate proline uptake by Human Dermal Fibroblast cells.

1. To 99.2 grams of sterile distilled water add 0.4 grams of Sodium Chloride and 0.4 grams of Magnesium Chloride. Stir at room temperature until the solids dissolve and a clear solution is obtained.
2. The solution obtained in Step 1 was split into 5 equal aliquots and stored in sterile test tubes.
3. Sample No. 1 was left untreated; to be used as a control to compare to the other treated samples.
4. Rod No. 232-1 (as supplied by Wekroma) was placed in the Wekroma Bio-Transfer device as shown in the accompanying drawing FIG. 1.
5. One of the test tubes containing the sterile salt solution was then passed through the Bio-Transfer as depicted in the accompanying drawing. This procedure was repeated two times. Then the sample was set aside.
6. Then Rod No. 232-1 was removed from the Bio-Transfer and Rod No. 232-2 was placed in the Bio-Transfer. Another of the test tubes containing the sterile salt solution was passed through the Bio-Transfer as in Step No. 5.
7. Repeat the above procedure until the remaining test tubes were treated, (Sample No. 4) was treated with Rod No. 232-3 and Sample No. 5 was treated with Rod No. 232-4). Rods No. 232-1, 2, 3 and 4 are identical replicas of each other.
8. All samples were submitted for proline uptake testing. The results indicate that all samples showed increases over the media control. Wekroma treated salt solutions (Samples Nos. 2 and 5) showed statistically significant increases over Sample No. 1 (salt solution, untreated by the Wekroma Bio-Transfer device).

The protocol for the proline uptake testing is as follows. Two confluent 24-well plates were treated with the sample solutions. The untreated salt solution control was added neat in 1, 5, and 10% concentrations Solutions of the same material was passed through Rod No. 232 and assayed at the same concentrations as the control. Each sample was assayed in triplicate. The samples were then labeled with 1 $\mu$Ci/ml Of $^3$H Proline by adding 1 $\mu$l to each ml well. Plates were incubated over a five day period, in which time the treatment procedure was repeated. After treatment incubation was complete, the plates were assayed for total protein uptake. Each plate was washed with 1 ml of ice cold PBS and then 1 ml of ice cold TCA for 10 minutes. TCA washes were repeated twice for five minutes each. Each plate was then washed with 1 ml of MeOH and allowed to dry. Protein was then solubilized in 0.3M NaOH and gently shaken for 0.5 hours. Supernatant is collected and added to scintillant, and measured on the liquid scintillation counter.

EXAMPLE 2

The following demonstrates how a specific mineral water treated with the Wekroma Bio-Transfer device can stimulate proline uptake by Human Dermal Fibroblast cells.

Body Booster mineral water having the composition listed in Table 1 was treated in a Wekroma Bio-Transfer device using a Wekroma Rod No. 232 as described in Example 1.

Three confluent 24-well plates were labelled with 1 $\mu$ci/ml of $^3$H Proline prior to the addition of the mineral water. Tests were conducted with the Body Booster mineral water that was treated with the Wekroma Bio-Transfer device, using the untreated mineral water as a control.

Each sample was assayed in triplicate using 0.1, 0.5 and 1% concentrations Plates were incubated over the weekend before being assayed for total protein. At this time each plate was washed with 1 ml of ice cold PBS, and then 1 ml of ice cold TCA for 10 minutes TCA washes were repeated twice for five minutes each. Each plate was then washed with 1 ml of MeOH and allowed to dry. Protein was then solubilized in 0.3M NaOH containing 1% SDS and gently shaken for 0.5 hours. Supernatant is collected and added to scintillant, and measured on the liquid scintillation counter.

Figure 2:
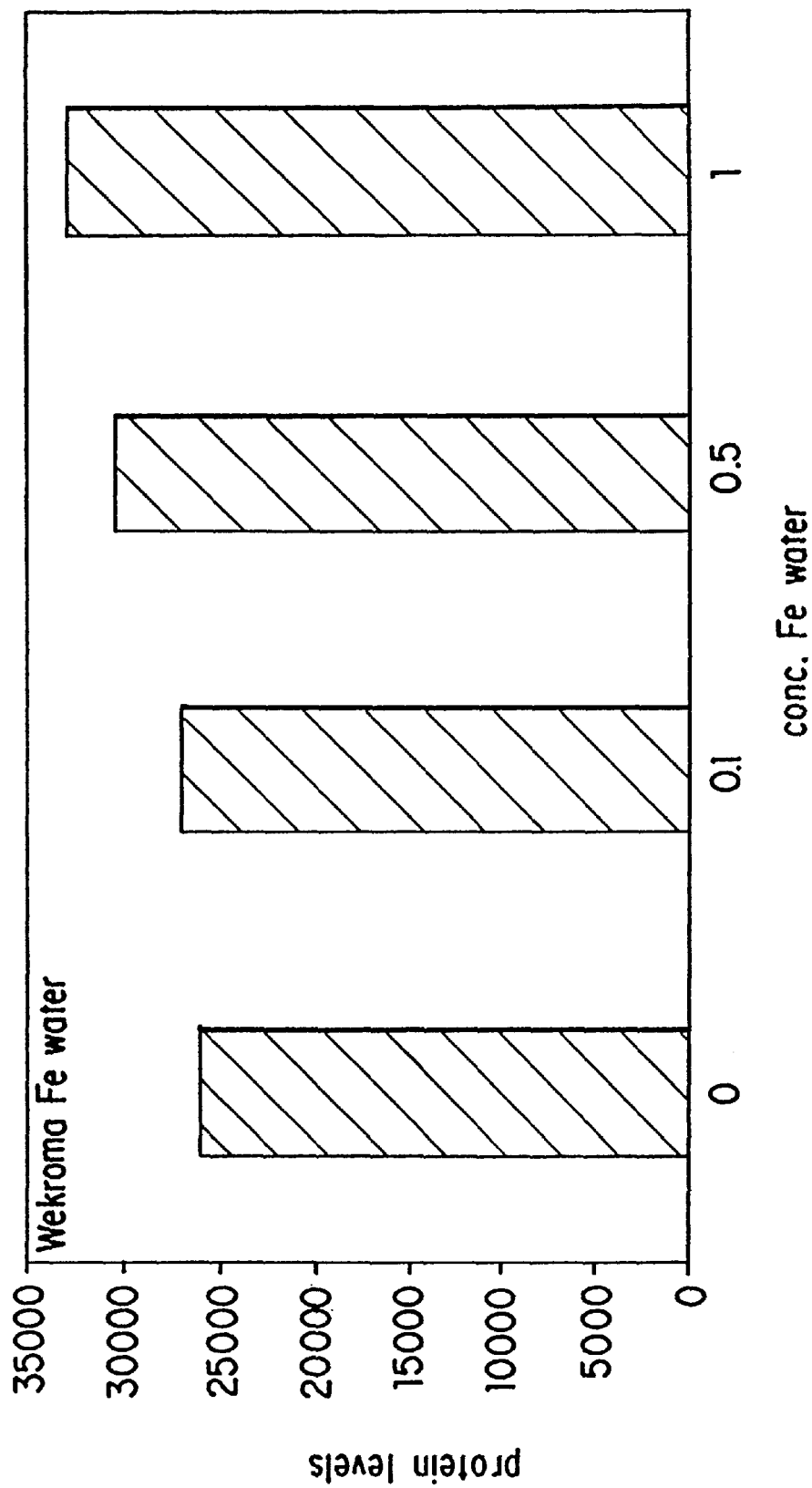
FIG. 2 depicts graphically the increase in proline level in Human Dermal Fibroblast calls upon increasing the concentration of the Body Booster mineral water that was treated with the Wekroma Bio-Transfer device.

An increase in protein count was observed for the Wekroma treated Body Booster mineral water. A dose dependent increase occurred in which the 0.1, 0.5, and 1% concentrations increased protein by 3, 17, and 27%, respectively. See Table 2 and FIG. 2. The results for the 0.5 and 1% doses were statistically significant with p-values of 0.02 and 0.03, respectively.

EXAMPLE 3

The following demonstrates that Body Booster mineral water by itself increases proline uptake However, treatment of this mineral water with the Wekroma Transfer device using Rod No. 232 as outlined in Example 1 resulted in higher it proline uptake compared to the untreated mineral water control. Treatment of this mineral water with the Wekroma Transfer device using Rod No. 1200.7 did not increase proline uptake beyond the control.

Two confluent 24-well plates were treated with the following: various different treatments of Body Booster consisting of Wekroma Rods Nos. 232 and 1200.7. The Body Booster control was added neat in 1, 5, and 10% concentrations. The same material was passed through Rods Nos. 232 and 1200.7 and assayed at the same concentrations Each sample was assayed in triplicate. The samples were then labeled with 1 $\mu$Ci/ml of $^3$H Proline by adding 1 $\mu$l to each ml well. Plates were incubated over a five day period, in which time the treatment procedure was repeated. After treatment incubation was complete, the plates were assayed for total protein uptake. Each plate was washed with 1 ml of ice cold PBS, and then 1 ml of ice cold TCA for 10 minutes TCA washes were repeated twice for five minutes each. Each plate was then washed with 1 ml of MeOH and allowed to dry. Protein was then solubilized in 0.3N NaOH and gently shaken for 0.5 hours. Supernatant is collected and added to scintillant, and measured on the liquid scintillation counter.

Body Booster increased uptake 52% when treated with Rods 232, yielding a 12% increase from the untreated groups, while 1200.7 treatment paralleled the untreated group. Student's t-test indicated that all the materials were statistically significant. See Table 3.

EXAMPLE 4

We repeated earlier experiments which showed that Body Booster mineral water increased proline incorporation Body Booster mineral water without any information transferred to it, increased proline uptake by 44, 38, and 33% at 1, 5, and 10% concentrations. See Table 4. In this experiment, information transferred with Nekroma Rods No. 1200.7 displayed a statistically significant increase of 16% at a 10% dosage.

Two confluent 24-well plates were treated with Body Booster mineral water that received 10 passes with Wekroma Rods No. 1200.7. The Body Booster mineral water control was added neat in 1, 5, and 10% concentrations. The same material was passed through Rods No. 232 and assayed using the equivalent concentrations. TGF $\beta$ (10 ng/ml) was assayed as a positive control. Each sample was assayed in triplicate The samples were then labeled with 1 $\mu$Ci/ml of $^3$H Praline by adding 1 $\mu$l to each 1 ml well. Plates were incubated over a five day period, in which time the treatment procedure was repeated. After treatment incubation was complete, the plates were assayed for total protein uptake. Each plate was washed with 1 ml of ice cold TCA for 10 minutes. TCA washes were repeated twice for five minutes each. Each plate was then washed with 1 ml of MeOH and allowed to dry. Protein was then solubilized in 0.3M NaOH and gently shaken for 0.5 hours. Supernatant was collected and added to scintillant, and measured on the liquid scintillation counter.

TGF $\beta$ displayed increases of 63%, and 87% (P(0.003). Body Booster mineral water increased uptake 44, 38, and 33% as a control at 1, 5, and 10% concentrations Body Booster mineral water treated with Rods No. 1200.7 (antioxidant) displayed increases of 6 and 16% at 5 and 10% concentrations respectively, when compared to Body Booster mineral water controls. Student's t-test conveyed statistical significance for all materials, when values were compared to untreated controls. Statistical analysis, compared to Body Booster mineral water control, yielded values greater than 0.05 excluding the 10% concentration that had been treated with Rod No. 120307

EXAMPLE 5

The following experiment showed that aqueous solutions so of sodium chloride and magnesium chloride treated with Wekroma Rod 232 increased collagen production by Normal Human Dermal Fibroblasts cells ("NHDF") to a significant degree compared to the control aqueous solution containing the same concentration of salts but untreated with the Wekroma Rod 232. The ability of the treated aqueous solutions to increase collagen production was retained upon storage of at least six months.

Five salt solutions of 0.4% NaCl and 0.4% MgCl$_2$ in deionized water were made. One solution (3249/1) was not treated with Wekroma Rod 232 and used as the control solution. The remaining four salt solutions (3249/2-3249/5) were treated with Nekroma Rod, 232-1, 232-2, 232-3, and 232-4 respectively. All of these Wekroma Rods are identical replicas of each other. All five salt solutions were assayed at three different doses (1, 5 and 10% in deionized water) for any increase in the production of collagen by NHDF cells.

All sample solutions showed increases, of varying degrees, over the media control (see % change column in Table 5). Wekroma treated salt solutions 3249/2 and 3249/5 showed statically significant increases, over 3249/1, in the amount of collagen released by KHDF cells in culture.

3249/1, the untreated control solution, showed increases in collagen production (over the media control).

The four salt solutions treated with the Wekroma Rod's 232 were sealed and stored under ambient conditions for six months and then reassayed for their ability to increase the production of collagen by NHDF cells. These "retained solutions" were also compared to stored solutions that were retreated with the Wekroma Rods 232 (labeled as "remake solutions").

The results of the assay of the control salt solution, retained solutions and remake solutions are shown in Table 6.

Collagen levels were not enhanced by the presence of 10% of the control salt solution ($MgCl_2$ and $NaCl_2$ in deionized $H_2O$). Media containing 10% remake solution treated with #232-Rod 4 resulted in a 36% increase in absolute collagen level, and a 6% decrease in DNA, combining to yield an overall increase in Collagen/DNA of 43% over the control salt solutions Retain solution originally treated with #232-Rod 4, when present at 10% concentration, yielded an increase of 14% in absolute collagen levels along with a 24% decrease in DNA, combining to yield an overall increase in Collagen/DNA of 50%. In contrast, Mimosa pudica, used as a positive control, increased absolute collagen level by 20%, and decreased DNA by 65%, which resulted in an overall increase in Collagen/DNA of 238%.

Of the sample solutions tested, the only ones to show substantial increases in collagen levels were the remake solution treated with #232-Rod 4 and the retain solution treated with #232 Rod-4. These samples yielded increases of 43 and 50% respectively (over the salt solution control). In this assay, the positive control, Mimosa pudica (@ 50 μg/ml), yielded an increase of 238% over the media control.

The following outlines the method used in the above two to determine collagen and DNA levels.

NHDF cells were seeded and grown to confluence in a 96 well plate prior to being treated with the Wekroma samples (n=3). Mimosa pudica (@ 50 μg/ml) was added as a positive control and media alone served as the negative control. The plate was incubated for 4 days at 37°C./5% $CO_2$ before the supernatants were harvested, and stored at −70° in siliconized tubes until the ELISA was performed.

The collagen ELISA was performed as follows:

A 96 well enzyme immunoassay grade microliter plate is coated, overnight at 4° C., with an optimal amount of Human Type 1 collagen. In a separate microliter plate (low protein binding) equal volumes of primary antibody (Rabbit anti Human Type 1 Collagen) is mixed with either the collagen standards or the unknowns and allowed to react overnight at 4° C. (Inhibition Step). The collagen standards or the collagen present in the unknowns will bind with the primary antibody, leaving some of the primary antibody unbound.

The collagen coated plate is then washed extensively with Phosphate Buffered Saline containing 0.05% Tween-20 (PBST)e dried and blocked with PBS containing 3% Bovine Serum Albumin for 1.5 hours at 37° C. The blocking solution is then removed from the wells, the plate is dried and the contents of the wells containing the primary antibody/standard or unknown solution are transferred to the blocked, collagen coated plate. The plate is incubated for 30 minutes at room temperature, to allow whatever primary anti-body is left unbound to free collagen, to bind to the collagen coating the plate. After the 30 minute incubation, the solution is discarded. Discarded in the solution will be the primary antibody bound to free collagen (from the standards or unknowns) Any primary antibody that did not bind to collagen during the inhibition step will be free to bind to the collagen coating the wells. If there was a lot of collagen present in the standard or unknown solution, most of the primary antibody will be bound up and not be available to bind to the collagen coating the wells.

The primary antibody bound to the collagen coating the well is detected by the addition of a goat anti-rabbit lgG-Alkaline Phosphatase conjugated antibody and incubating for 1.5 hours at room temperature followed by extensive washing with PBST. The alkaline phosphatase present in the wells is detected by the addition of p-Nitrophenyl Phosphate as a substrate and the optical densities are read at 405 nM on a Molecular Devices microplate reader. A standard curve is constructed and the collagen levels of the unknowns are determined from this curve.

The DNA assay was performed as follows. DNA levels are determined by performing a freeze/thaw lysis of the cells in the presence of water and adding Hoechst 33258 (a dye that binds to DNA and becomes fluorescent) The plate is then read on the spectrophotometer and DNA levels are calculated from the standard curve.

EXAMPLE 6

It is possible to produce a substrate treated only with a magnetic vector potential field without the application of any information energy. This can be accomplished by, for example, passing a solution through the Wekroma Bio-Transfer device without the placement of any rods within the device. Such a treated substrate is capable of improving skin condition upon administration of the substrate to the skin.

It should be apparent to one of ordinary skill that other embodiments not specifically disclosed nonetheless fall within the scope and spirit of the present invention. Hence, the descriptions herein should not be taken as limiting the invention in any way, except as stated in the following claims.

All references cited above are hereby expressly incorporated by reference.

TABLE 1

| Composition Of Body Booster Mineral Water | |
|---|---|
| Aluminum | 1–10% |
| Arsenic | 0 |
| Antimony | 0 |
| Barium | 0 |
| Beryllium | 0.01–0.1% |
| Boron | 0.01–0.1% |
| Bismuth | 0 |
| Cadmium | 0 |
| Calcium | 10–100% |
| Chromium | 0 |
| Cobalt | 0 |
| Copper | 0.01–0.1% |

TABLE 1-continued

Composition Of Body Booster Mineral Water

| | |
|---|---|
| Iron | 0.01–0.1% |
| Lead | 0 |
| Lithium | 0 |
| Magnesium | 1–10% |
| Manganese | 1–5% |
| Mercury | 0 |
| Molybdenum | 0 |
| Niobium | 0 |
| Nickel | 0.01–0.1% |
| Phosphorus | 0 |
| Potassium | 0 |
| Sodium | 0.1–1.0% |
| Silicon | 0.01–1.0% |
| Silver | 0 |
| Strontium | 0.1–1.0% |
| Tantalum | 0 |
| Tellurium | 0 |
| Tin | 0 |
| Titanium | 0.01–0.1% |
| Tungsten | 0 |
| Vanadium | 0 |
| Zinc | <0.01% |
| Zirconium | 0 |

TABLE 2

| MATERIAL | | average DPM | % change | P-value |
|---|---|---|---|---|
| untreated | control | 29666.67 | | |
| Fe H2O | 0.10% | 30266 | 2.020225 | |
| | 0.50% | 28933.33 | −2.47191 | |
| | 1% | 31395 | 5.825843 | |
| treated | control | 26077.33 | | |

TABLE 2-continued

| MATERIAL | | average DPM | % change | P-value |
|---|---|---|---|---|
| Fe H2O | 0.10% | 26974.33 | 3.439769 | 0.49 |
| | 0.50% | 30508.67 | 16.99305 | 0.02 |
| | 1% | 33053.33 | 26.7512 | 0.03 |

TABLE 3

| | | dpm | avg. dpm | % change | P-value | % change from BB control |
|---|---|---|---|---|---|---|
| BB-control | 1% | 105215 | | | | |
| | | 110134 | 109543.3 | 34.19933 | 0.001 | |
| | | 113281 | | | | |
| | 5% | 95021 | | | | |
| | | 117246 | 107548.3 | 31.75529 | 0.02 | |
| | | 110378 | | | | |
| | 10% | 95786 | | | | |
| | | 99194 | 98260.33 | 20.37675 | 0.001 | |
| | | 99801 | | | | |
| BB-232 | 1% | 111191 | | | | |
| | | 125587 | 123668.3 | 51.50358 | 0.003 | 12.89444 |
| | | 134227 | | | | |
| | 5% | 122170 | | | | |
| | | 110580 | 117679 | 44.16617 | 0.001 | 9.419641 |
| | | 120287 | | | | |
| | 10% | 95146 | | | | |
| | | 104946 | 100037 | 22.55331 | 0.004 | 1.808122 |
| | | 100019 | | | | |
| BB-12007 | 1% | 104023 | | | | |
| | | 112237 | 109372.3 | 34.08511 | 0.002 | −0.1561 |
| | | 111857 | | | | |
| | 5% | 109353 | | | | |
| | | 108673 | 113090.7 | 38.64361 | 0.003 | 5.153342 |
| | | 121246 | | | | |
| | 10% | 106709 | | | | |
| | | 100710 | 96776.33 | 18.64304 | 0.12 | −1.51027 |
| | | 82910 | | | | |

TABLE 4

| | | dpm | avg. dpm | % change | P-value | dpm minu avg.contro | P-value among BB |
|---|---|---|---|---|---|---|---|
| control | | 36335 | | | | | |
| | | 30925 | 32558 | | | | |
| | | 30414 | | | | | |
| TGF B | | 51288 | | | | | |
| | | 58159 | 53015.67 | 62.83453 | 0.003 | | |
| | | 49600 | | | | | |
| BB-C | 1% | 48752 | | | | 16194 | |
| | | 44941 | 46925 | 44.1274 | 0.003 | 12383 | |
| | | 47082 | | | | 14524 | |
| | 5% | 49367 | | | | 16809 | |
| | | 41801 | 44988.33 | 38.17904 | 0.01 | 9243 | |
| | | 43797 | | | | 11239 | |
| | 10% | 39432 | | | | 6874 | |
| | | 50542 | 43245.67 | 32.82655 | 0.06 | 17984 | |
| | | 39763 | | | | 7205 | |
| BB-232 | 1% | 41992 | | | | 9434 | |
| | | 46412 | 45608 | 40.08231 | 0.01 | 13854 | 0.58 |
| | | 48420 | | | | 15862 | |
| | 5% | 45920 | | | | 13362 | |
| | | 44642 | 46858.33 | 43.92264 | 0.005 | 12084 | 0.54 |
| | | 50013 | | | | 17455 | |
| | 10% | 44162 | | | | 11604 | |
| | | 43276 | 43928.67 | 34.92434 | 0.004 | 10718 | 0.86 |
| | | 44348 | | | | 11790 | |
| control | | 28578 | | | | | |
| | | 25524 | 29228.67 | | | | |
| | | 33584 | | | | | |
| TGF B | | 51548 | | | | | |

TABLE 4-continued

|  |  | dpm | avg. dpm | % change | P-value | dpm minu avg.contro | P-value among BB |
|---|---|---|---|---|---|---|---|
|  |  | 57206 | 54718.33 | 87.20776 | 0.001 |  |  |
|  |  | 55401 |  |  |  |  |  |
| BB-1200.7 | 1% | 44480 |  |  |  | 15251.33 |  |
|  |  | 42907 | 42945.33 | 46.92881 | 0.005 | 13678.33 | 0.67 |
|  |  | 41449 |  |  |  | 12220.33 |  |
|  | 5% | 45415 |  |  |  | 16186.33 |  |
|  |  | 52041 | 47527.33 | 62.6052 | 0.005 | 22812.33 | 0.14 |
|  |  | 45126 |  |  |  | 15897.33 |  |
|  | 10% | 49850 |  |  |  | 20621.33 |  |
|  |  | 49835 | 50052.33 | 71.24398 | 0.001 | 20606.33 | 0.05 |
|  |  | 50472 |  |  |  | 21243.33 |  |

TABLE 5

PRODUCTION OF COLLAGEN BY NHDF CELLS EXPOSED TO SAMPLE SOLUTIONS

| Sample | pg/ml +/− S.D. | % Change | p value |
|---|---|---|---|
| 3249/1 |  |  |  |
| Control salt |  |  |  |
| solution |  |  |  |
| 10% | 2.5 +/− 0.02 | 4.2 |  |
| 5% | 2.7 +/− 0.03 | 12.5 |  |
| 1% | 2.6 +/− 0.01 | 8.3 |  |
| 3249/2 |  |  |  |
| 10% | 3.0 +/− 0.06 | 25 | 0.02 |
| 5% | 2.8 +/− 0.07 | 17 | 0.1 |
| 1% | 2.4 +/− 0.12 | 0 | 0.8 |
| 3249/3 |  |  |  |
| 10% | 2.6 +/− 0.02 | 8.3 | 0.1 |
| 5% | 2.7 +/− 0.06 | 12.5 | 0.2 |
| 1% | 2.8 +/− 0.11 | 17 | 0.2 |
| 3249/4 |  |  |  |
| 10% | 2.7 +/− 0.09 | 12.5 | 0.1 |
| 5% | 2.7 +/− 0.09 | 12.5 | 0.8 |
| 3249/5 |  |  |  |
| 10% | 3.5 +/− 0.04 | 46 | 0.002 |
| 5% | 3.0 +/− 0.05 | 25 | 0.02 |
| TBFβ | 3.0 +/− 0.02 | 25 |  |
| Media Control | 2.4 +/− 0.01 |  |  |

TABLE 6

PRODUCTION OF COLLAGEN BY NHDF CELLS EXPOSED TO RETAIN AND REMAKE SOLUTIONS

| Sample | Coll (μg/ml) | % Change | DNA (μg/ml) | % Change | Coll/DNA | % Change |
|---|---|---|---|---|---|---|
| Media | 0.15 +/− 0.001 |  | 6.2 +/− 0.3 |  | 0.024 |  |
| M. pudica | 0.18 +/− 0.008 | +20 | 2.2 +/− 0.1 | −65 | 0.081 | 238 |
| Control salt soln. | 0.14 +/− 0.006 |  | 5.0 +/− 0.11 |  | 0.028 |  |
| #232-Rod 4 remake | 0.19 +/− 0.015 | +36 | 4.7 +/− 0.08 | −6 | 0.040 | +43 |
| #232-Rod 4 retain | 0.16 +/− 0.023 | +14 | 3.8 +/− 0.09 | −24 | 0.042 | +50 |
| #232-Rod 1 retain | 0.15 +/− 0.012 | +7 | 4.6 +/− 0.07 | −8 | 0.033 | +18 |
| #232-Rod 2 | 0.14 +/− 0.018 | 0 | 6.5 +/− 0.02 | +30 | 0.021 | −25 |

TABLE 6-continued

PRODUCTION OF COLLAGEN BY NHDF CELLS
EXPOSED TO RETAIN AND REMAKE SOLUTIONS

| Sample | Coll (μg/ml) | % Change | DNA (μg/ml) | % Change | Coll/DNA | % Change |
|---|---|---|---|---|---|---|
| retain #232-Rod 3 retain | 0.15 +/- 0.015 | +7 | 5.2 +/- 0.07 | +4 | 0.029 | +3 |
| #232-Rod 3 remake | 0.16 +/- 0.01 | +14 | 4.6 +/- 0.12 | -8 | 0.035 | +25 |
| BQ Rod BQ-DAT-C4 | 0.14 +/- 0.002 | 0 | 4.4 +/- 0.06 | -12 | 0.032 | +14 |

We claim:

1. A method of improving skin condition comprising the steps of:
   a) exposing a physiologically acceptable substrate to a magnetic vector potential field and directly applying information energy to the substrate while the substrate is exposed to the magnetic vector potential field to produce a substrate that contains information energy; and
   b) administering to the skin the substrate that contains information energy, resulting in increased protein synthesis by the skin.

2. The method of claim 1 where at least one Wekroma Rod selected from the group consisting of 1200.7, 622, 232, 7509, 326, 329, Fibro 1, and Fibro 2 is used to directly apply information energy to the substrate.

3. The method of claim 2 where at least one Wekroma Rod No. 232 is used to directly apply information energy to the substrate.

4. The method of claim 3 wherein the substrate is at least once passed through a Wekroma Bio-Transfer device that produces the magnetic vector potential field and that contains at least one Wekroma Rod No. 232.

5. A method of improving skin condition comprising the steps of:
   a) exposing a physiologically acceptable substrate to a magnetic vector potential field; and
   b) administering to the skin the exposed substrate, resulting in increased protein synthesis by the skin.

6. The method of claim 5 or 1 further resulting in increased collagen content of the skin.

7. The method of claims 5 or 1 wherein the substrate is in the gaseous, liquid, solid or liquid crystalline phase.

8. The method of claim 7 wherein the substrate is in the liquid or liquid crystalline phase.

9. The method of claim 8 wherein the substrate is in the liquid phase.

10. The method of claim 8 wherein the liquid phase comprises water.

11. The method of claim 10 wherein the liquid phase comprises sodium chloride and magnesium chloride.

12. The method of claim 10 wherein the liquid phase comprises iron ions and calcium ions.

13. The method of claims 5 or 1 wherein the magnetic vector potential field is produced by two opposite sets of magnets, each said set of magnets comprising a plurality of magnets arranged side by side, with alternating N and S poles, wherein the substrate is exposed to a magnetic vector potential field when the substrate is placed between the opposing sets of magnets.

14. The method of claim 13 wherein the substrate is at least once passed through a Wekroma Bio-Transfer device.

* * * * *